US00PP35104P2

(12) United States Plant Patent
Cornelis

(10) Patent No.: US PP35,104 P2
(45) Date of Patent: Apr. 11, 2023

(54) ***SPATHIPHYLLUM* PLANT NAMED 'CORSPAVAR2'**

(50) Latin Name: ***Spathiphyllum* sp. Schott**
Varietal Denomination: CORSPAVAR2

(71) Applicant: Daniel Cornelis, Melsen (BE)

(72) Inventor: Daniel Cornelis, Melsen (BE)

( * ) Notice: Subject to any disclaimer, the term of this patent is extended or adjusted under 35 U.S.C. 154(b) by 2 days.

(21) Appl. No.: 17/803,414

(22) Filed: Jun. 27, 2022

(51) Int. Cl.
*A01H 5/02* (2018.01)
*A01H 6/10* (2018.01)

(52) U.S. Cl.
USPC ..... Plt./364

(58) Field of Classification Search
USPC ..... Plt./364
See application file for complete search history.

*Primary Examiner* — Susan McCormick Ewoldt
(74) *Attorney, Agent, or Firm* — Samuel R. McCoy, Jr.

(57) ABSTRACT

'CORSPAVAR2' is a new and distinctive *Spathiphyllum* plant which is characterized by a compact growth habit, an abundance of narrow-elliptic foliage with moderately undulated leaf margins, dark green and glossy foliage that is irregularly flecked with light greyed-green in an irregularly pinnate pattern, white spathes which become progressively suffused with yellow-green as they age which creates a variegation pattern similar to that of the foliage, and the stability of all characteristics from generation to generation.

4 Drawing Sheets

Latin name of the genus and species: The Latin name of the genus and species of the novel variety disclosed herein is *Spathiphyllum* sp. Schott.

Variety denomination: The inventive variety of *Spathiphyllum* disclosed herein has been given the variety denomination 'CORSPAVAR2'.

BACKGROUND OF THE INVENTION

Parentage: 'CORSPAVAR2' is a seedling selection which resulted from the controlled pollination of *Spathiphyllum* sp. 'Domino' (U.S. Plant Pat. No. 9,944), and the pollen parent, *Spathiphyllum* sp. 'Alfa CD' (U.S. Plant Pat. No. 10,823). Said cross was performed by the inventor at a commercial greenhouse in Melsen-Merelbeke, Belgium in the year 2000. After approximately one and a half years of evaluating the seedlings that resulted from said cross, the new cultivar was first noted for its unique foliage variegation and was subsequently isolated for further evaluation in order to confirm the distinctness and stability of the characteristics first observed. After approximately twenty years of evaluation, the new *Spathiphyllum* plant was selected for commercialization and given the name 'CORSPAVAR2'.

Asexual Reproduction: Asexual reproduction of 'CORSPAVAR2' was first accomplished by way of vegetative division was first performed in the autumn of 2001 at a commercial greenhouse in Melsen-Merelbeke, Belgium, and later by meristematic tissue culture micropropagation. Numerous successive generations so produced have shown that the unique features of the instant cultivar are stable and reproduced true to type.

SUMMARY OF THE INVENTION

The cultivar 'CORSPAVAR2' has not been observed under all possible environmental conditions and the phenotype may vary somewhat with variations in the instant environment such as temperature, day length, and light intensity, without, however, any variance in genotype. The following characteristics have. been repeatedly observed and represent the distinguishing characteristics of the new *Spathiphyllum* cultivar 'CORSPAVAR2'. These traits, in combination, distinguish 'CORSPAVAR2' as a new and distinct cultivar.

1. *Spathiphyllum* 'CORSPAVAR2' exhibits a compact growth habit, with an abundance of narrow-elliptic foliage with moderately undulated leaf margins; and
2. *Spathiphyllum* 'CORSPAVAR2' exhibits glossy, dark green foliage that is irregularly flecked with light greyed-green in a pinnate pattern; and
3. *Spathiphyllum* 'CORSPAVAR2' exhibits white spathes held above the foliage.
4. *Spathiphyllum* 'CORSPAVAR2' exhibits spathes that become progressively suffused with yellow-green, creating an irregular pinnate pattern similar to that of the foliage, with age.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
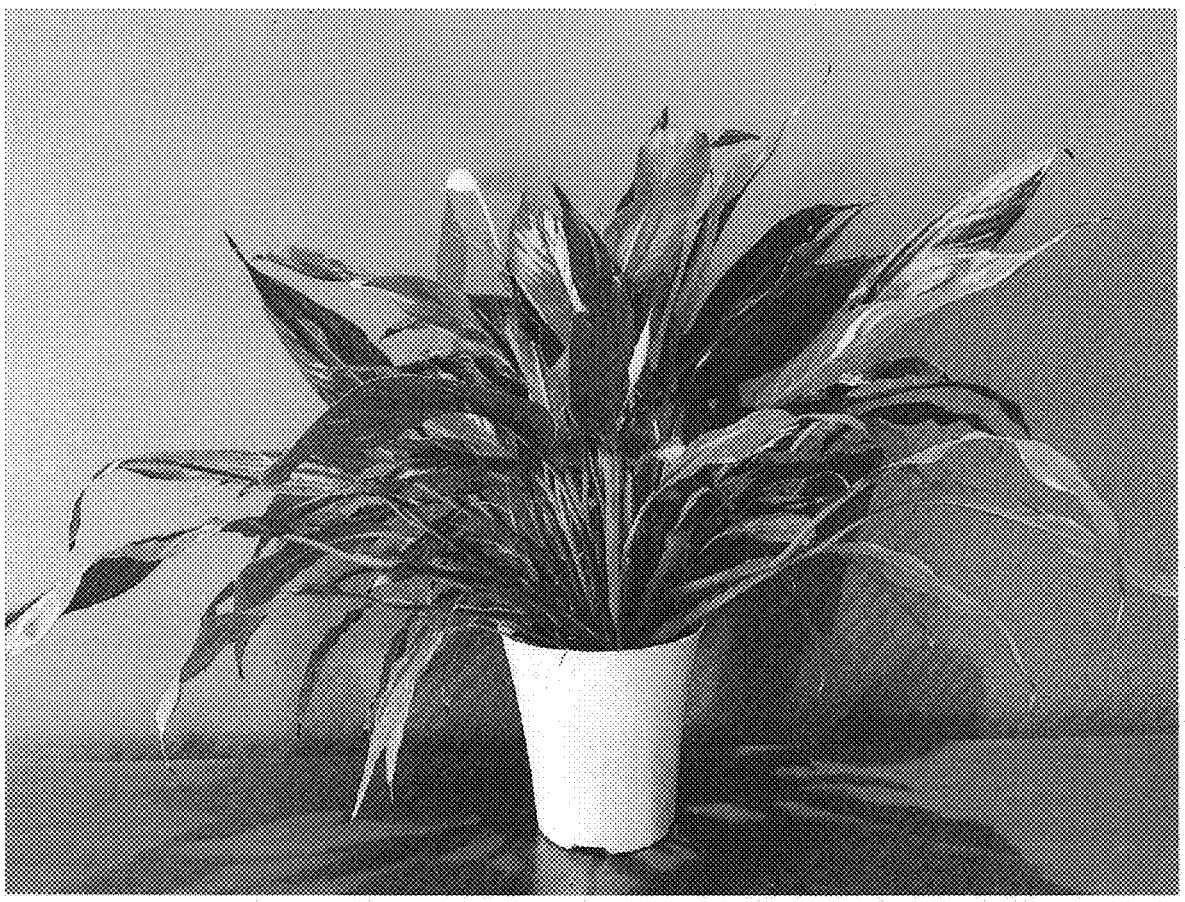
FIG. 1 shows, as nearly true as it is reasonably possible to make the same in color illustrations of this type, the typical foliage and growth characteristics of the new cultivar, 'CORSPAVAR2'. The plant shown is approximately 8 months old from a rooted cutting, potted into a 15 cm nursery pot, grown in a climate-controlled greenhouse in Homestead, Fla.
Figure 2:
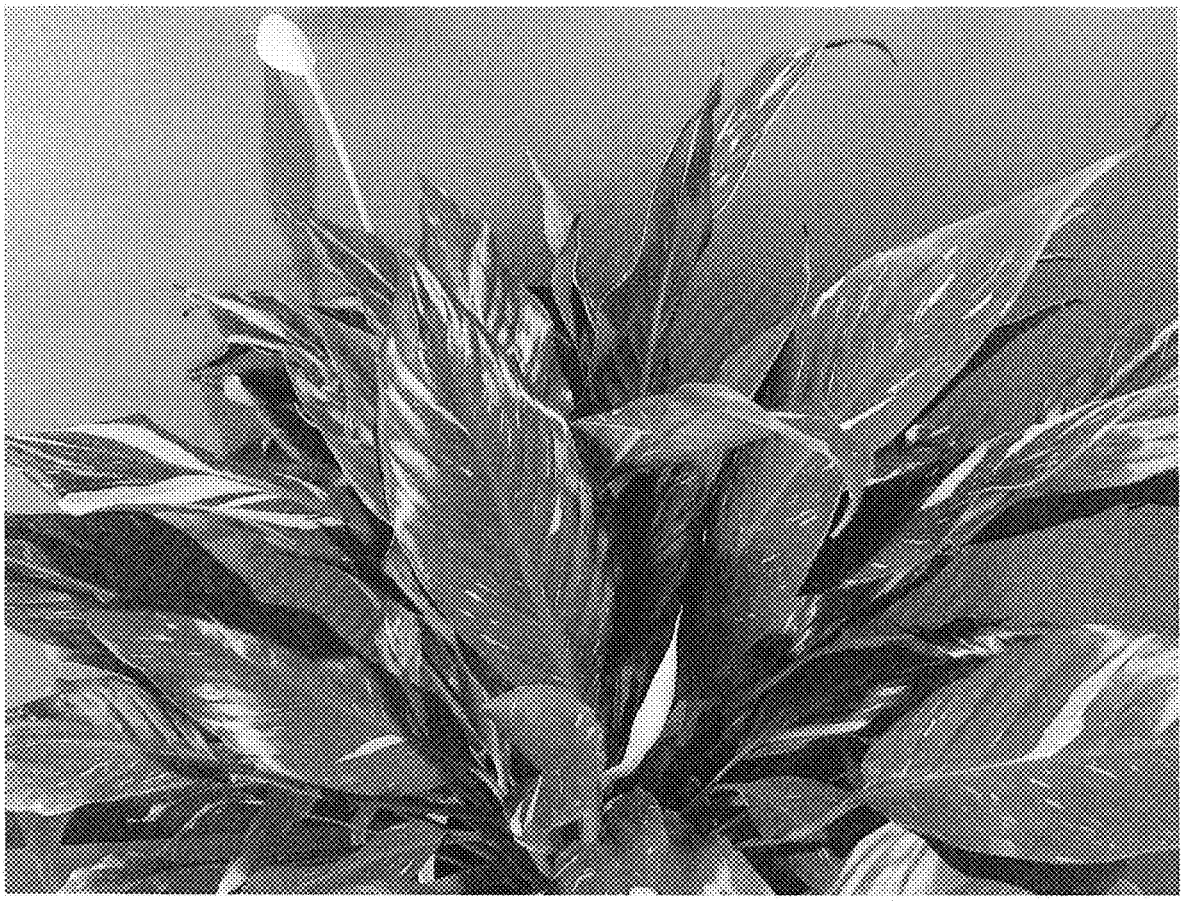
FIG. 2 shows, as nearly true as it is reasonably possible to make the same in color illustrations of this type, the typical mature foliage of 'CORSPAVAR2'.
Figure 3:
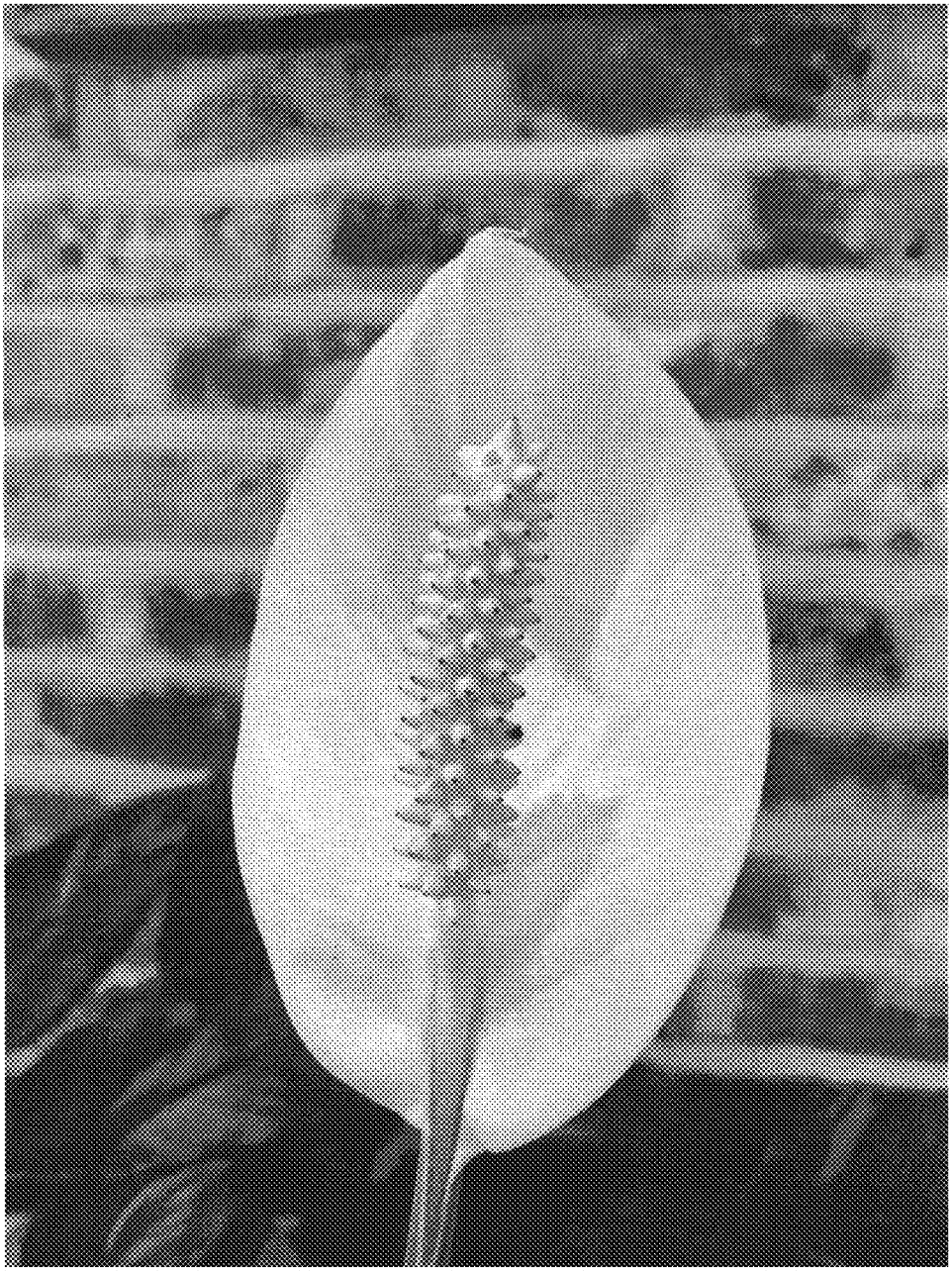
FIG. 3 shows, as nearly true as it is reasonably possible to make the same in color illustrations of this type, the typical spathe of 'CORSPAVAR2'.
Figure 4:
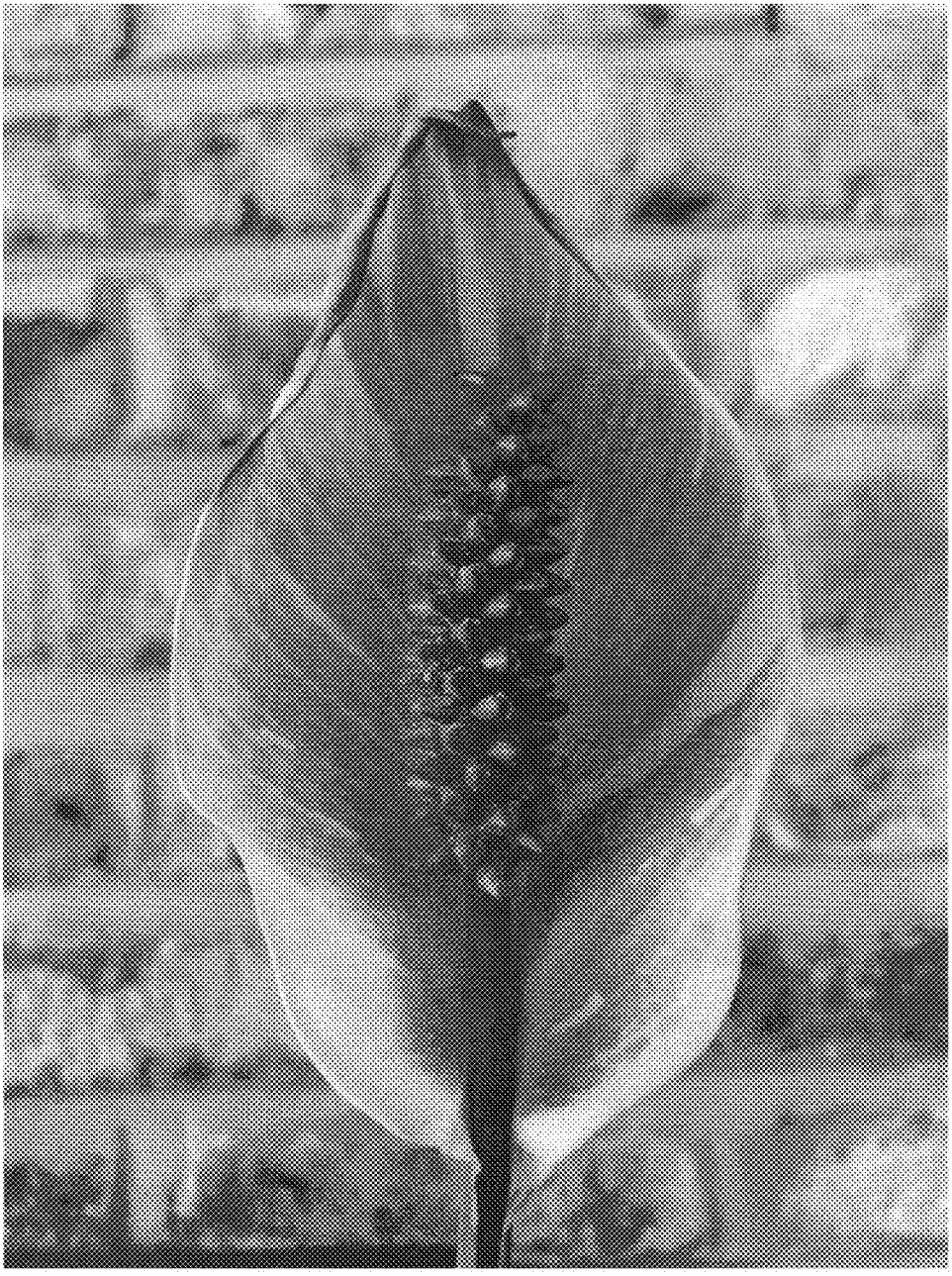
FIG. 4 shows, as nearly true as it is reasonably possible to make the same in color illustrations of this type, the typical spathe of 'CORSPAVAR2'.

The following observations and measurements made in December of 2021 describe 42-week-old 'CORSPAVAR2' plants grown in 15 cm nursery containers at a commercial greenhouse in Homestead, Fla. The growing substrate had an Electrical Conductivity of 1.0 and a pH of 6.5. Plants were top-dressed with a 18-6-8 fertilizer at 14 grams per container at the time of planting. Plants were produced using conventional greenhouse production protocols for *Spathiphyllum* which consisted of 30,000 lux of light exposure, regular overhead irrigation, applications every two to three days of a complete fertilizer at an Electrical Conductivity level of 2.0 to 2.5, and an application of gibberellic acid to induce flowering. Ambient temperatures range from 65 to 100 degrees Fahrenheit. Chemical pest and disease control measures were taken as needed. No photoperiodic treatments or artificial light was given to the plants.

Those skilled in the art will appreciate that certain characteristics will vary with older or, conversely, with younger plants. 'CORSPAVAR2' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, Sixth Edition.

A botanical description of 'CORSPAVAR2' and comparisons with the parent and the most similar variety of common knowledge are provided below.

General plant description:

*Growth habit.*—Clump forming; broad spreading to upright with foliage arising directly from the base of each clump.

*Plant profile.*—Broad obovate with inflorescences carried within and slightly above the foliage.

*Height.*—49.0 cm in height, to the highest leaf; 60.0 cm to top of highest spathe.

*Width.*—Average 76.5 cm in width.

*Growth Rate.*—Moderately fast growing.

*Plant vigor.*—Moderately to highly vigorous.

*Propagation.*—Method — Meristematic tissue culture. Time to initiate roots — Approximately 28 days to initiate roots at approximately 21 degrees Centigrade. Crop time — Approximately 32 weeks to produce a well-rooted 15 cm container from a rooted cutting.

*Environmental tolerances.*—Moderately high tolerance to rain and wind; tolerant of temperatures ranging from 5 to 40 degrees Celsius. Cold hardy to USDA Hardiness Zone 10.

*Pest resistance and susceptibility.*—Plants have not been observed to be any more or less susceptible or resistant to pathogens and pests common to *Spathiphyllum.*

Root system: Moderately fibrous, not fleshy; moderately dense.

Stems:

*Branching characteristics.*—Clumping plant with leaves emerging directly from the base of the plant; no lateral branching.

Foliage:

*Arrangement.*—Alternate; equitant.

*Division.*—Simple.

*Attachment.*—Petiolate.

*Quantity of leaves per shoot.*—Most mature shoot with 15 leaves; 11 on average.

*Quantity of shoots per plant.*—Average of 6 mature shoots.

*Quantity of leaves per plant.*—Approximately 60 to 70.

*Lamina.*—Shape — Narrowly elliptic. Apex — Apiculate. Base — Attenuate. Aspect — Slightly carinate and slightly reflexed; leaves occasionally exhibit a slight to moderate axial twist. Attitude — Petioles nearest to the center of the plant are upright to near vertical and become progressively more relaxed towards the outer foliage; geniculum bends to an approximate angle of 30 to 50 degrees to the petiole which, as a result, orients the lamina in a nearly horizontal plane. Dimensions — 27.0 cm long and 7.0 cm wide, on average. Margin — Entire; moderately coarsely undulate. Texture and luster, adaxial surface — Smooth and glabrous; glossy. Texture and luster, abaxial surface — Smooth and glabrous; moderately glossy. Juvenile color, adaxial surface — Green, nearest to RHS 137C, and becoming progressively more suffused with yellow-green towards the base, RHS 144C; irregularly flecked with light green, nearest to in between RHS 138C and 138D, in a somewhat-pinnate pattern. Juvenile color, abaxial surface — Green, nearest to in between RHS 138A and 138B; irregularly flecked with light green, nearest to RHS 138D, in a somewhat-pinnate pattern. Mature color, adaxial surface — Green, nearest to in between RHS 137A and 139A; irregularly flecked with light greyed-green, nearest to RHS 195D, in a somewhat-pinnate pattern. Mature color, abaxial surface — Green, nearest to in between RHS 138A and 138B; irregularly flecked with light greyed-green, nearest to RHS 196C, in a somewhat-pinnate pattern. Venation — Vein pattern — Pinnate. Vein color, adaxial surface — Green, nearest to RHS 138A. Vein color, abaxial surface — Nearest to in between green and yellow-green, RHS 138A and 144A.

*Petiole, excluding geniculum.*—Aspect — Ovoid at the base and becoming near-terete at the geniculum. Length — 21.3 cm, on average; longest observed petiole is 28.5 cm. Width — Approximately 0.35 cm at the geniculum and 0.55 cm wide and 0.75 cm deep at the base. Color, adaxial surface — Green, nearest to RHS 137B. Color, abaxial surface — Green, nearest to RHS 137B. Texture and luster — Smooth, glabrous, and matte. Strength — Strong. Geniculum — Length — 4.2 cm, on average. Width — 0.35 cm, on average; ranging from 0.3 to 0.55 cm. Texture and Luster — Smooth, glabrous and matte. Color, adaxial surface — Green, nearest to RHS 138A. Color, abaxial surface — Green, nearest to RHS 137C. Petiole wings — Length — Approximately 33.0 cm. Width — Approximately 1.3 cm. Color — Green, nearest to in between RHS 137A and 139A;

irregularly flecked with light greyed-green, nearest to RHS 195D, in a somewhat-pinnate pattern.

Inflorescence:

*Type.*—Spathe.

*Arrangement.*—Peduncles arise directly from the base of the plant with spathes carried above the foliar plane.

*Attitude.*—Near vertical.

*Dimensions.*—11.4 cm long, excluding the peduncle, and 5.15 cm wide; spathe is 2.1 cm deep.

*Flowering habit.*—Continuous.

*Natural flowering season.*—Spring and autumn in the norther hemisphere, with occasional flowering in summer.

*Time to flowering.*—24 weeks from planting.

*Fragrance.*—Faint, sweet and pleasant (typical *Spathiphyllum* scent).

*Self-cleaning or persistent.*—Persistent.

*Flower longevity.*—Flowers stay in good condition approximately 3 weeks on the plant.

*Peduncle.*—Attitude — Near vertical. Length — 54.4 cm. Diameter — 0.5 cm. Strength — Strong. Texture and luster — Smooth, glabrous and matte. Color — Nearest to in between green and yellow-green, RHS 138B and 144A.

Spathe:

*Attitude.*—Near vertical.

*Aspect.*—Slightly to moderately conclave.

*Length.*—Approximately 18.6 cm.

*Width.*—Approximately 6.6 cm.

*Depth.*—4.3 cm.

*Shape.*—Elliptic to ovate.

*Margin.*—Entire; slightly coarsely undulate.

*Apex.*—Apiculate.

*Base.*—Long attenuate.

*Texture, inner and outer surfaces.*—Glabrous, slightly coriaceous.

*Luster, inner and outer surfaces.*—Inner surface is moderately glossy; outer surface is glossy.

*Color.*—Inner surface, when opening — White, nearest to RHS 155C, and tipped yellow-green, nearest to RHS 145A. Outer surface, when opening — White, nearest to RHS NN155C, and tipped yellow-green, nearest to RHS 145A; main vein is yellow-green, RHS 144C. Inner surface, at maturity — White, nearest to RHS NN155D, and tipped yellow-green, nearest to. RHS 145A; main vein is green-white, nearest to RHS 157C. As spathes age, they become progressively suffused with yellow-green, creating an irregular pinnate pattern similar to that of the foliage, nearest to in between RHS 144B and 144C. Outer surface, at maturity — White, nearest to RHS NN155D, and tipped yellow-green, nearest to RHS 145A; main vein is yellow-green, RHS 144C. As spathes age, they become progressively suffused with yellow-green, creating an irregular pinnate pattern similar to that of the foliage, nearest to in between RHS 144B and 144C.

Spadix:

*Attitude.*—At an average angle of 25 degrees to the peduncle.

*Shape.*—Oblong, columnar.

*Apex.*—Obtuse.

*Base.*—Obtuse.

*Length.*—Approximately 6.2 cm.

*Width.*—Approximately 1.25 cm.

*Color.*—When opening — Greyed-yellow, nearest to RHS 160C. Mature — Greyed-yellow, nearest to RHS 160D, and becoming green, RHS 141A, with age.

*Flowers.*—General — Flowers are. greatly diminished, to the point of being largely indistinguishable and immeasurable. Quantity of flowers per spadix — Approximately 150. Arrangement — Spirally placed on spadix. Shape — Rounded. Diameter — Approximately 0.4 cm. Height — Approximately 0.2 cm.

Reproductive organs:

*General.*—Reproductive organs are greatly diminished, to the point of being largely indistinguishable and immeasurable.

*Anthers.*—Not observed.

*Stigma.*—Quantity — 1. Shape — Conical. Dimensions — 0.2 cm tall and 0.2 cm in diameter. Color — Greyed-yellow, nearest to RHS 160D.

Seed and fruit: Seed production has not been observed.

Comparisons with the parent: Plants of the new cultivar 'CORSPAVAR2' may be distinguished from the seed parent, *Spathiphyllum* sp. 'Domino' (U.S. Plant Pat. No. 9,944), by the following combination of characteristics:

1. 'CORSPAVAR2' exhibits a foliage color that is darker green when compared to the foliage color of 'Domino'.
2. 'CORSPAVAR2' exhibits more prominent foliage variegation relative to 'Domino', with a greater occurrence of the light greyed-green flecking.
3. 'CORSPAVAR2' exhibits a slower rate of growth, relative to 'Domino'.

Plants of the new cultivar 'CORSPAVAR2' may be distinguished from the pollen parent, *Spathiphyllum* sp. 'Alfa CD' (U.S. Plant Pat. No. 10,823), by the following combination of characteristics:

1. 'CORSPAVAR2' exhibits smaller, narrower foliage relative to 'Alfa CD'.
2. 'CORSPAVAR2' exhibits dark green foliage with light greyed-green flecking in an irregularly pinnate pattern, whereas the foliage of 'Alfa CD' is solid green.
3. 'CORSPAVAR2' exhibits white spathes which become progressively suffused with yellow-green as they age, creating a variegation pattern similar to that of the foliage, whereas the spathes of 'Alfa CD' remain white as they age.
4. 'CORSPAVAR2' exhibits a slower rate of growth, relative to 'Alfa CD'.

Comparisons with the most similar variety of common knowledge:

Plants of the new cultivar 'CORSPAVAR2' may be distinguished from the commercial variety *Spathiphyllum* sp. 'Corspabont' (U.S. Plant Pat. No. 14,151) by the following combination of characteristics:

1. 'Corspabont' exhibits more prominent foliage variegation relative to 'CORSPAVAR2', with a greater occurrence of the light greyed-green flecking.
2. 'CORSPAVAR2' exhibits a slower rate of growth, relative to 'Corspabont'.

That which is claimed is:

1. A new and distinct variety of *Spathiphyllum* plant named 'CORSPAVAR2', substantially as described and illustrated herein.

* * * * *